US006306913B1

(12) United States Patent
Hayes et al.

(10) Patent No.: US 6,306,913 B1
(45) Date of Patent: Oct. 23, 2001

(54) CONTAINER FOR 4-ALLYLANISOLE AND ANALOG SCOLYTID PESTICIDES

(75) Inventors: Jane L. Hayes, La Grande, OR (US); Brian L. Strom, Alexandria; Lawrence M. Roton, Pollock, both of LA (US); Leonard L. Ingram, Jr., Starkville, MS (US); Edgar R. Butts, Fairfield, CT (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/218,273

(22) Filed: Dec. 21, 1998

Related U.S. Application Data

(63) Continuation-in-part of application No. 09/073,778, filed on May 6, 1998, now abandoned, which is a continuation-in-part of application No. 08/932,810, filed on Sep. 16, 1997, now abandoned, which is a division of application No. 08/625,978, filed on Apr. 1, 1996, now Pat. No. 5,695,807, which is a continuation-in-part of application No. 08/358,707, filed on Dec. 19, 1994, now Pat. No. 5,518,757, which is a continuation-in-part of application No. 08/113,709, filed on Aug. 31, 1993, now Pat. No. 5,403,863.

(51) Int. Cl.[7] .......................... A01N 25/00; A01N 25/08; A01N 25/18; A01N 31/14; A01N 37/08
(52) U.S. Cl. .......................... 514/689; 514/699; 514/717; 514/731; 514/764; 514/919; 514/953; 514/957; 424/84; 424/405; 424/408; 424/409; 424/411; 424/412; 424/456; 424/DIG. 10; 43/1; 43/125; 43/126; 43/129; 473/569; 473/577; 106/15.05
(58) Field of Search .................... 424/405, 408, 424/409, DIG. 10, 84, 411, 412, 456; 514/717, 919, 689, 699, 731, 764, 953, 957; 273/317; 124/1; 102/501, 502; 473/569, 577, 609; 43/1, 125, 126, 129; 106/15.05

(56) References Cited

U.S. PATENT DOCUMENTS

| | | | |
|---|---|---|---|
| 3,655,129 | 4/1972 | Selner | 239/60 |
| 3,755,064 | 8/1973 | Maierson | 428/338 |
| 3,855,105 | 12/1974 | Diveley | 204/157.69 |
| 3,876,762 | 4/1975 | Rabussier et al. | 53/503 |
| 4,017,030 | 4/1977 | Coplan et al. | 239/44 |
| 4,137,273 | 1/1979 | Siddall | 568/648 |
| 4,170,631 | 10/1979 | Young et al. | 424/419 |
| 4,176,189 | 11/1979 | Itaya et al. | 514/389 |
| 4,219,570 | 8/1980 | Inazuka et al. | 514/731 |
| 4,272,398 | 6/1981 | Jaffe | 427/213.31 |
| 4,405,360 | 9/1983 | Cardarelli | 504/323 |
| 4,590,282 | 5/1986 | Henrick | 549/453 |
| 4,690,825 | 9/1987 | Won | 424/501 |

(List continued on next page.)

OTHER PUBLICATIONS

Aldrich, Catalog Handbook of Fine Chemical Company, Wisconsin, pp. 46 and 119, 1988.*

Hayes, et al., "Repellent Properties of the Host Compound 4–Allylanisole to the Southern Pine Beetle", *Journal of Chemical Ecology*, 20(7): 1595–1615 (1994).

Hayes, et al., "Identification of a Host Compound and It's Practical Applications: 4–allylanisole as a Bark Beetle Repellent", Paper presented at Southern Station Chemical Sciences Meeting; Feb. 1–2, 1994; Starkville, MS.

Gries, et al., "New Techiques for Capturing and Analyzing Semiochemicals for Scolytid Beetles (Coleoptera: Scolytidaie)", *Journal of Economic Entomology*, 81(6):1715–1720 (1988).

Liu, et al., "Volatiles from the Foliage of Soybean, *Glycine max*, and Lima Bean, *Phaseolus lunatus*: Their Behavioral Effects on the Insects *Trichoplusia ni* and *Epilachna varivestis*", *Journal of Agric. Food Chem.*, 37:496–501 (1989).

Hayes, J.L., "New Patent for Protecting Pines from Bark Beetle Infestation in Urban and Rural Areas", Forestry Report, R8–FR–55, Jan. 1996.

Werner, Richard A., "Response of the Beetle *Ips grandicollis* to Combnations of Host and Insect Produced Attractants", *Journal of Insect Physiol.*, 18:1403–1412.

Werner, Richard A., "Aggregation Behavior of the Beetle *Ips grandicollis* in Response to Host–Produced Attractants", *Journal of Insect of Physiol.*, 18:423–437.

Hayes, J.L. and B.L. Strom, "4–Allylanisole as an Inhibitor of Bark Beetle (Coleoptera: Scolytidae) Aggregation", *Forest Entomology*, 87(6) :1586–1594 (1994).

Hayes, et al., "Suppression of Bark Beetles and Protection of Pines in the Urban Environment: A Case Study", Journal of Arboriculture, 22(2):67–74 (1996).

(List continued on next page.)

Primary Examiner—John Pak
(74) Attorney, Agent, or Firm—Evelyn M. Sommer; Patterson, Belknap Webb & Tyler

(57) ABSTRACT

A projectile can be used to administer pesticides such as one or more from the group consisting of 4-allylanisole, anisole, allylbenzene, 4-isopropylanisole, p-anisaldehyde, ethylbenzene, cumene, 4-methoxyacetophenone, 4-methylstyrene, 2-propylphenol, phenetole, and toluene, for scolytid infestation. Conifers, which are a target for scolytids, are protected by the application of the pesticides by use of a projectile containing the compound which explodes upon contact with the conifer thereby emitting the compound.

5 Claims, No Drawings

U.S. PATENT DOCUMENTS

| | | | |
|---|---|---|---|
| 4,713,200 | 12/1987 | Blade | 554/218 |
| 4,732,899 | 3/1988 | Gehret et al. | 514/215 |
| 4,774,081 | 9/1988 | Flashinski et al. | 514/617 |
| 4,782,094 | 11/1988 | Numata et al. | 514/721 |
| 4,839,383 | 6/1989 | Vite | 514/456 |
| 4,855,127 | 8/1989 | Abrutyn et al. | 424/411 |
| 4,880,624 | 11/1989 | Metcalf et al. | 424/84 |
| 4,886,545 | 12/1989 | Peck et al. | 504/358 |
| 5,116,862 | 5/1992 | Weston et al. | 514/436 |
| 5,162,367 | 11/1992 | Blade et al. | 514/465 |
| 5,250,574 | 10/1993 | Sakamoto et al. | 514/721 |
| 5,273,996 | 12/1993 | Dickens et al. | 514/450 |
| 5,281,418 | 1/1994 | Lindgren et al. | 424/405 |
| 5,303,496 * | 4/1994 | Kowalkowski | 43/1 |
| 5,314,693 | 5/1994 | Suga | 424/196.1 |
| 5,403,863 | 4/1995 | Hayes et al. | 514/717 |
| 5,418,164 | 5/1995 | Andersch et al. | 435/254.1 |
| 5,518,757 | 5/1996 | Hayes et al. | 427/4 |
| 5,532,029 * | 7/1996 | Fuerst et al. | 428/35.7 |
| 5,695,801 | 12/1997 | Hayes et al. | 427/4 |

OTHER PUBLICATIONS

Werner, Richard A., "Toxicity and Repellency of 4–Allyanisole and Monoterpenes from White Spruce and Tamarack to the Spruce Beetle and Eastern Larch Beetle (Coleopetra: Scolytidae)", 24 (2) :372–379 (1995).

Hayes, et al., "Repellency of the Host–Produced Compound 4–Allylanisole and Its Analogs to Conifer–Feeding Bark Beetles (Coleopetera: Scolytidae)", Abstract fro poster session presented at the $14^{th}$ Annual Meeting, ISCE, Jul. 12–16, 1997, Vancouver, British Columbia, Canada.

Aldrich Catalog Handbook of Fine Chemicals, Aldrich Chemical Co., Inc., Milwaukee, WI, 1988, p. 46.

CAB Abstract 90:83480 (1990).

* cited by examiner

CONTAINER FOR 4-ALLYLANISOLE AND ANALOG SCOLYTID PESTICIDES

CROSS-REFERENCE TO RELATED APPLICATIONS

This application is a Continuation-in-Part of Ser. No. 09/073,778, filed May 6, 1998, now abandoned, which is a Continuation-in-Part of Ser. No. 08/932,810 filed Sep. 16, 1997, now abandoned, which is a Divisional of Ser. No. 08/625,978 filed Apr. 1, 1996 and issued as U.S. Pat. No. 5,695,807 on Dec. 9, 1997, which is a Continuation-in-Part of Ser. No. 08/358,707 filed Dec. 19, 1994 and issued as U.S. Pat. No. 5,518,757 on May 21, 1996, which is a Continuation-in-Part of Ser. No. 08/113,709 filed Aug. 31, 1993 and issued as U.S. Pat. No. 5,403,863 on Apr. 4, 1995.

STATEMENT REGARDING FEDERALLY SPONSORED RESEARCH

Applicable. The United States of America as represented by the Secretary of the Agriculture is a co-owner of this application.

BACKGROUND TO THE INVENTION

Infestation of conifers by insect pests of the beetle family Scolytidae is well documented. Insect attacks on healthy, damaged, or weakened host trees continue to be a significant commercial and ecological problem. Trees that are susceptible to infestation by scolytids include loblolly pines, eastern and western white pines, eastern and western yellow pines, Norway spruce, larch, eastern redcedar, eastern hemlock, Fraser fir, Douglas fir, and other fir trees.

Certain chemical insecticides have been employed for limited protection of trees. However, the use of synthetic chemical insecticides in insect control raises serious concerns about the adverse environmental and ecological effects these agents may have. Often, organic pesticides are more costly than naturally occurring products and the effective control of insects by means of an insecticidal agent typically requires relatively extensive application of the insecticide to targeted susceptible surfaces of the host tree. Because insecticides are generally nonspecific in their toxicity and are typically applied by broadcast application, e.g. aerial or high power sprayers, their use is associated with a significant risk of harm to non-target organisms, such as natural enemies of scolytids, as well as bees and other pollinators. Chlorpyrifos for example is a registered insecticidal compound used in scolytid control that has a longer residual impact on natural enemies of scolytids than on scolytids.

In an effort to avoid the use of insecticides, researchers have devoted considerable attention to the development of cost-effective repellents derived from naturally occurring products for the control of scolytid infestations. As a result, they have developed both chemical and microbial agents capable of keeping pests from harming a plant by either repelling or attacking the pests, pesticides.

For instance, U.S. Pat. Nos. 5,403,863, 5,518,757 and 5,695,807, which are incorporated by reference herein, disclose methods for repelling scolytids using the scolytid-repelling compound 4-allylanisole or a selected analog (anisole, allylbenzene, 4-isopropylanisole, p-anisaldehyde, ethylbenzene, cumene or 4-methoxyacetophenone), and mixtures thereof. 4-allylanisole is a naturally occurring compound found in the resin exuded by a potential host tree susceptible to infestation by scolytids. An important advantage to the use of 4-allylanisole or its analogs in scolytid control is that effective protection may be obtained without spraying all surfaces. Scolytid control may be achieved by applying the compound directly as a concentrated liquid, powder, or vapor to a portion of the tree to be protected. Because it does not require uniform application, pesticides such as those disclosed in this family of patents and applications may be applied in a packaged delivery container, such as a pre-filled projectile (e.g., a so-called "paint ball," although it should be appreciated that any container that emits the contents upon contact—even if not released for free flight or otherwise restrained—should be considered a projectile for purposes of this application) which delivers the desired compound by emission after contacting a portion of the tree (which will, for convenience, be termed an "explosion" although it need not be a sudden and instantaneous discharge). In this way, a pesticide, can be applied at a high enough level on the tree—which may exceed 50 feet—for proper effectiveness; in the case of those pesticides disclosed herein, such heights may be in the range of 2–3 feet to 20–30 feet, as appropriate for the pest and the pesticide, which will be easily determinable by those skilled in the art based upon the pest to be targeted. Also, the repellent compound may be carried on elution devices placed proximate to the tree. The repellent compound may be impregnated in a polymer mass, such as by being encased in a suitable polymer for delivery as a pre-filled projectile, or microencapsulated in a suitable polymer. The repellent compound could be delivered onto or in proximity with a surface to be protected by placing the polymer mass or the microencapsulated repellent in proximity with the surface.

There is a need to develop alternative scolytid repellents to those currently in use.

BRIEF SUMMARY OF THE INVENTION

In one embodiment, the present invention is a container for delivering a pesticide, e.g., for repelling scolytids from a surface subject to attack by the scolytids.

The present invention is also a method for repelling scolytids from a surface subject to attack by scolytids comprising the following steps: (a) providing a repellent comprising a compound selected from the group consisting of 4-allylanisole, anisole, allylbenzene, 4-isopropylanisole, p-anisaldehyde, ethylbenzene, cumene, 4-methoxyacetophenone, 4-methylstyrene, 2-propylphenol, phenetole, and toluene and mixtures thereof; and (b) applying an effective dose of the repellent onto or in proximity with the surface. The repellent may be applied as a liquid, powder, or vapor directly onto, or in proximity with, the surface to be protected.

Another embodiment of the present invention is a method for repelling scolytids from a surface subject to attack by scolytids comprising the steps of: (a) providing a container containing a compound selected from the group consisting of 4-allylanisole, anisole, allylbenzene, 4-isopropylanisole, p-anisaldehyde, ethylbenzene, cumene, 4-methoxyacetophenone, 4-methylstyrene, 2-propylphenol, phenetole, and toluene, or mixtures thereof, in an amount sufficient to repel at least 50% of insects in the family Scolytidae; (b) contacting the container with the surface; and (c) allowing the repellent to be dispersed from the container onto or in proximity with the surface in an amount effective to repel scolytids.

It is understood to one skilled in the art that the above embodiments may include the use of carriers, stickers, adjuvants, markers, and the like to increase the effectiveness of the repellent for use in particular applications and/or to identify the application sites of the pesticide.

Additionally, the container for delivering pesticides may optionally be used together with bait or other materials that may either serve to attract or repel to intended target of the pesticide.

It is an object of the present invention to provide an environmentally and ecologically sound method of protecting susceptible surfaces against attack by scolytids.

Other objects, advantages and features of the present invention will become apparent after examination of the specification, claims and drawings.

DETAILED DESCRIPTION OF THE INVENTION

In one embodiment the present invention is a scolytid repellent comprising a compound selected from the group consisting of 4-allylanisole, anisole, allylbenzene, 4-isopropylanisole, p-anisaldehyde, ethylbenzene, cumene, 4-methoxyacetophenone, 4-methylstyrene, 2-propylphenol, phenetole, and toluene, and mixtures thereof.

Each of the scolytid-repelling compounds of this invention may be obtained in a variety of manners, including isolating the compound from a natural source, synthesizing the compound using methods known to one skilled in the art of organic chemistry, or purchasing it through a commercial supplier.

The effectiveness of each insect repellent of the present invention is preferably evaluated, as described below, by means of a laboratory assay (see also Hayes, et al., *J. Chem. Ecol.* 20:1595–1615, 1994; Hayes and Strom, *J. Economic Entomology* 87:1586–1594, 1994). The scolytid-repelling abilities of 4-methylstyrene and toluene were also confirmed in field trials that included 4-allylanisole and five additional 4-allylanisole analogs, as detailed in the Examples below.

By "an amount of repellent effective to repel scolytids" we mean that amount of repellent that when applied directly or indirectly to a surface, or in proximity with a surface, results in an effective vapor dose of the repellent at or proximate to the surface. An "effective vapor dose" is a repellent vapor concentration that achieves effective repellency, causing a significant increase in the number of scolytids repelled from the surface to be protected, relative to the number of scolytids repelled from surfaces treated with a suitable control carrier lacking the repellent. Preferably, at least about 50% of the scolytids exposed to the repellent are repelled. The amount of repellent needed to achieve an effective vapor dose depends on a number of factors, including environmental conditions, such as rain and wind, which may carry off or degrade the repellent, and repeated application of the repellent may be required.

The present invention is also a method for protecting surfaces susceptible to scolytid infestation through the direct or indirect application of an amount of repellent effective to repel scolytids, wherein the repellent comprises a compound selected from the group consisting of 4-allylanisole, anisole, allylbenzene, 4-isopropylanisole, p-anisaldehyde, ethylbenzene, cumene, 4-methoxyacetophenone, 4-methylstyrene, 2-propylphenol, phenetole, and toluene, and mixtures thereof.

Preferably the insect to be repelled is a member of the genus Ips or Dendroctonus.

The repellent can be prepared as a neat preparation (i.e., a preparation composed of 100% repellent, with no additives), as a powder, admixed with an environmentally compatible carrier. The repellent can be prepared as a solid wick or polymer mass (e.g., polyurethane) impregnated with the repellent compound which is released therefrom. The repellent can be microencapsulated in a suitable polymer microcapsule, such as a polyurea microcapsule, from which the repellent is released over a period of time, or it can be encapsulated in a container or projectile from which the repellent is released upon direct or indirect contact. Application of sprays and prepared suspensions to trees may also be effective. A minimum effective concentration of the compound may be 0.01 percent, but greater concentrations can be employed. Concentrations of up to 100 percent may be employed to achieve an effective vapor dose release rate.

The compounds are typically used in the lowest possible concentration needed to achieve effective repellency. In some situations, higher concentrations may be necessary or desirable. Factors to be considered include repellency rate, method of treatment, local weather conditions, stage and size of infestation, and other factors known to those of skill in the art.

Mixtures of the compounds of the invention may also be used. It is within the ability of one of ordinary skill in the art to prepare mixtures, taking into account the desired repellency rate, product cost, treatment method, scolytid and conifer species targeted for treatment, and other factors known to those of skill in the art.

Alternatives to the invention disclosed and described above, particularly with respect to concentrations, environmentally compatible carriers, and methods of administration, are within the spirit and scope of the present invention.

The following nonlimiting examples are intended to be purely illustrative.

EXAMPLES

1. Methods

Laboratory Assay for Effectiveness of Repellent

To test the effectiveness of compounds in repelling scolytids, a previously published laboratory assay was employed (Hayes, et al., *J. Chem. Ecol.* 20:1595–1615, 1994; Hayes, et al., In J. Vozzo [ed.] Research and applications of chemical sciences in forestry: Proceeding of the 4th Southern Station Chemical Sciences Meeting, GTR-SO-104:69–80, 1994). The candidate compound was applied as a circle (17 cm in diameter by 5 mm in width) to a 28 by 21.5 cm piece of uncoated cardboard using a camel-hair brush. Three minutes after application, a beetle was placed in the center of the circle. In each trial, at least 20 healthy-appearing beetles were tested. Testing was conducted at room temperature (22°–25° C.) with light supplied from an adjoining room. The beetles were briefly refrigerated prior to testing to reduce their tendency to fly immediately upon release. An object was used to cast a shadow over the test circle in order to minimize response to light, which could interfere with the interpretation of insect response to an applied substance.

Following the release of an insect, the insect was exposed to the compound for a 30-second period, during which time insect response was observed and recorded as nonrepelled or repelled, and a numerical score assigned for the degree of the behavioral response.

Beetles that were not repelled appeared unfazed and walked through or proceeded across the circle within the 30 second assessment period. A repelled beetle exhibited one or more clearly observable behaviors, including stopping abruptly, raising its antennae, rearing up on its hind legs, standing motionless, or moving away from the circle.

Field Assays of the Effectiveness of Repellents

Field assays were carried out with selected 4-allylanisole analogs, including 4-allylanisole, anisole, 4-isopropylanisole, allylbenzene, 4-methylstyrene, toluene, and trans-anethole. The protocol for these assays is similar to that previously described (Hayes, et al., 1994a; Hayes and Strom, 1994c, both incorporated by reference as if fully set forth herein). Populations of local southern pine beetle were tested for response to these compounds using baited Lindgren funnel (16-funnel) traps. Traps were placed in or near active infestations of southern pine beetle over the course of the summer of 1997. Treatment baits consisted of the attractant frontalure and frontalure plus the test compound released from a 4-ml Samco pipette bulb. Hayes, et al., (In J. Vozzo [ed.] Research and applications of chemical sciences in forestry: Proceeding of the 4th Southern Station Chemical Sciences Meeting, GTR-SO-104:69–80, 1994) Frontalure is a combination of frontalin, which is an aggregation pheromone of the southern pine beetle, and a-pinene, a synergistic host oleoresin compound. In most cases, each trap array consisted of a total of six traps: one frontalure-only treatment; one frontalure plus 4-allylanisole treatment; and four traps containing treatments of frontalure plus a 4-allylanisole analog. In one instance a 12-trap array was employed, the array having two traps per treatment.

Release rates were determined in preliminary studies using simple gravimetric measurement of bulbs to provide elution in mg/day units. Release rates of all analog compounds were equal to or greater than that of 4-allylanisole. Placement of treatments was originally assigned at random and rotated sequentially with each collection. Each array was collected through two full rotations. Whole traps were moved in order to eliminate the possibility of contamination. Collection cups contained a 5.5×2 cm piece of pest strip, containing as its active ingredient the insecticidal agent 2,2 dichlorovinyldimethylphosphate to kill the captured insects. The numbers of captured southern pine beetle and of predatory clerid beetle *Thanasimus dubius*, the most important natural enemy of the southern pine beetle, were determined. Data were analyzed using ANOVA (SAS PROC GLM) to determine if the mean numbers of southern pine beetles or clerids were affected by treatment. The positions of the traps were also taken into consideration in the model.

2. Results

Laboratory Assay

The results of the laboratory testing are summarized in Table 1. Those compounded marked by an asterisk ("*") in the behavioral rating column were among those originally tested using a sample size of 45–53 beetles; this information is published in Hayes, et al., (In J. Vozzo [ed.] Research and applications of chemical sciences in forestry: Proceeding of the 4th Southern Station Chemical Sciences Meeting, GTR-SO-104:69–80, 1994). The percentage of scolytids repelled by 4-methylstyrene was about 70%; 2-propylphenol, phenetole, and toluene each repelled greater than 50% of scolytids. (These compounds are bolded in Table 1.) Each of these compounds elicited an obvious or dramatic repelled behavioral response from the test beetles.

TABLE 1

| ANALOG | % REPELLED | BEHAVIORAL RATING |
|---|---|---|
| anisole | >80 | * |
| allybenzene | >90 | * |
| trans-anethole | <20 | * |
| 4-isopropylanisole | >90 | * |
| 4-methoxycinnamonitrile | <20 | * |
| 4-methoxypheylacetonitrile | <30 | * |
| eugenol | <40 | * |
| 2-methylanisole | 35 | 1 |
| 4-methylanisole | 45 | 2 |
| p-anisaldehyde | 65 | 3 |
| ethylbenzene | 72 | 3 |
| butylbenzene | 39 | 2 |
| propylbenzene | 17 | 1 |
| cumene (= isopropylbenzene) | 55 | 3 |
| 2-methoxybenzyl alcohol | 0 | 1 |
| 3- | 0 | 1 |
| 4- | 0 | 1 |
| 2-methoxyacetophenone | 8 | 2 |
| 3- | 8 | 2 |
| 4- | 96 | 3 |
| 4-vinylanisole | 24 | 2 |
| m-xylene | 34 | 2 |
| o-xylene | 46 | 2 |
| p-xylene | 50 | 2 |
| toluene | 54 | 2 |
| 4-methylstyrene | 70 | 2 |
| 2-ethoxyanisole | 40 | 2 |
| p-cymene | 28 | 2 |
| 2-ethylphenol | 50 | 2 |
| 2-propylphenol | 55 | 2 |
| phenetole (= ethoxybenzene) | 55 | 2 |
| 4-tert-butylanisole | 0 | 1 |
| 2-propylanisole | 8 | 2 |

Twelve tested compounds performed as well as or better than the repellence standard in repelling greater than 50% of the beetles tested. Twenty-two other closely related structural analogs were found to be ineffective in repelling the southern pine beetle. An effort was made to screen analogous chemical compounds that previous studies had shown to be biologically active in attracting or repelling arthropods in other systems, such as corn rootworm and Drosophila. Analysis of test results together with chemical structures of the tested compounds has not revealed an essential characteristic of the chemical structure of an effective bark beetle repellent. It is therefore not possible to predict on the basis of structure which compounds will make good repellents.

Field Testing

Nine field trials were begun, of which three were terminated prior to completion because of the undue influence in captures caused by infestation of adjacent trees. Of the six completed trials, two did not meet the criterion of mean separation for frontalure alone and frontalure plus 4-allylanisole, a criterion which must be met in order for the trial to be considered a good assessment of the repellency performance of the compounds. However, even those trials that did not meet the mean separation criterion showed that frontalure alone was either the first or second most attractive of the tested compounds, whereas 4-allylanisole was shown to be the least attractive of the tested compounds. In all trials, 4-allylanisole captured the fewest beetles. Mean capture numbers varied between trials from fewer than 10 for any treatment to greater than 20 for all treatments, with the high number being an average of greater than 110 beetles attracted to frontalure. With log transformation of the number of southern pine beetles captured, five of the six completed arrays showed significant treatment effects. No array showed significant positional effects or treatment by position interactions. Simultaneous direct comparison of all analogs was not possible given space limitations in appropriate study sites. However, a comparison of the rank order of the repellency of the tested compounds from each trial showed that field testing results were generally consistent with those obtained in laboratory assays.

For each trial, the relative repellencies of the tested compounds were ranked from one to six (Table 2) with one being the best repellent. Interestingly, 4-methylstyrene and toluene, which elicited modest repellent response in laboratory tests, ranked second and third to 4-allylanisole in reduction of trap captures in the two field trials in which they were tested. These two compounds also have the highest elution rates; the high efficacy of these compounds relative to other 4-allylanisole analogs may be due in part to the high elution rates.

An important feature of the repellents of this invention is that the repellents do not repel or otherwise affect the clerid beetle Thanasimus dubius, a natural enemy of the scolytid beetle. These results demonstrate that these compounds provide an excellent alternative to insecticides because they do not interfere with naturally-occurring scolytid predators. Thus, these compounds are biologically-efficient conifer-protectants.

3. Application by Projectile

It will be appreciated that the pesticides of the instant invention, which may include repellents, may be applied in a single dose, such as by contacting a pesticide containing explosive-type projectile (which is to say, a projectile which will release its contents upon contact with a surface, but which does not necessarily contain an explosive charge) with a surface, thereby releasing the repellent upon contact (preferably without harming the surface). A simple, and readily available, example of this is a so-called "paint ball" containing the pesticide. A paint ball containing the pesticide, instead of paint, would be formulated to contain a specific amount of the pesticide. The paint ball would be applied to the site by loading it in a paint ball gun, aiming it at the target and shooting.

Paint balls are well known items used in outdoor sports, where one contestant tries to shoot the other with a paint-containing projectile using commonly available gun-like devices that allow the user to point and aim. Paint balls have, within the last several years, become an industry in the United States. The balls are typically fired from air ($CO_2$) powered guns and are primarily used in tournaments where teams wearing protective clothing fire upon each other. Commercially available paint ball gun devices and paint balls are well known, and are manufactured by companies such as Brass Eagle, DSDS and Perfect Circle Paint Balls.

The paint balls are generally comprised of an outer shell and an inner supply of paint. The usual paint ball size is that of a large marble and weighs just over 3 grams. The paint within the ball normally weighs between 2.5 to 2.75 grams and is brightly colored. Even though the balls are not very heavy, they retain a rigid circular form so as to pass through an air gun and air without deforming significantly. Paint balls have a range of over 100 yards using standard equipment. The outer shell of the paint ball is made from gelatin; however, specialty balls are made from a variety of plastics depending on the substances used within the balls.

Gelatin shells are used to enclose substances that are non-polar (hydrophobic), whereas most specialty plastic shells allow for both polar and non-polar substances. Petrochemicals are the major type of substances not compatible with the specialty plastic shells.

Paint balls are typically made with machinery containing an injection wedge that forces paint against the shell that is then forced through two rotating dies (wheels). The rotating wheels then seal the paint within the shells as they drop from the wedge/die apparatus. In this way paint, or for purposes of this invention pesticides/repellents, may be encased in the shell.

Application of product using a paint ball would: allow placement of the pesticide at heights that would otherwise require more use of ladders or other means of elevation, thereby adding labor and risks to the applicator that must climb the ladder; reduce the labor required and cost of treatment; improve the accuracy of pesticide placement; and reduce environmental exposure to pesticides. The paint ball technology clearly lends itself to the delivery of volatile compounds to trees for protection from insect pests such as the beetle. Use of a paint ball containing pesticides would allow selective application, by aiming and shooting pesticides at a desired target, e.g., a tree. optionally, a marker such as paint or dye can be included with a projectile to indicate where repellent has been applied.

TABLE 2

| Compound | 4-allylanisol | 4-isopropyl-anisole | allylbenzene | anisole | 4-methyl-styrene | toluene | trans-anethole | frontalure |
|---|---|---|---|---|---|---|---|---|
| mg/day release rate | 15.6 | 16.45 | 128.2 | 52.2 | 674.75 | 462.6 | 44.65 | 17.6 |
| TRIAL | rank | | | | | | | |
| 1 | 1 | 4 | 5 | 3 | — | 2 | — | 6 |
| 2 | 1 | 2 | 5 | 4 | — | 3 | — | 6 |
| 3 | 1 | 2 | — | 4 | 2 | — | 3 | 6 |
| 4 | 1 | 5 | — | 2 | 3 | — | 4 | 6 |
| 5 | 1 | 3 | 2 | 5 | — | — | 4 | 6 |
| 6 | 1 | 2 | 4 | 3 | — | — | 6 | 5 |
| mean rank | 1.0 | 3.5 | 4.0 | 3.5 | 2.5 | 2.5 | 4.25 | 5.8 |

We claim:

1. A container for delivering pesticide to a surface subject to Scolytidae infestation to repel conifer-feeding beetles in the family Scolytidae comprising an outer circular shell which encloses an inner supply of at least one compound selected from the group consisting of 4-allylanisole, anisole, allylbenzene, 4-isopropylanisole, p-anisaldehyde, ethylbenzene, cumene, 4-methoxyacetophenone, 4-methylstyrene, 2-propylphenol, phenetole, toluene and mixtures thereof, said container emitting an effective vapor dose of said compound upon contact with said surface at an appropriate height for utilizing the compound as a pesticide.

2. The pesticide container of claim 1, wherein the container is a paint ball.

3. The pesticide container of claim 2, further comprising a marker for indicating the area where some contact has been made with the surface.

4. The pesticide container of claim 1 wherein said outer shell is made from gelatin.

5. The pesticide container of claim 1 wherein said surface is a tree.

* * * * *